United States Patent [19]

Ten Haken et al.

[11] 4,399,149
[45] Aug. 16, 1983

[54] FUNGICIDES

[75] Inventors: Pieter Ten Haken, Eastling, Near Faversham; Thomas W. Naisby; Andrew C. G. Gray, both of Sittingbourne, all of England

[73] Assignee: Shell Oil Company, Houston, Tex.

[21] Appl. No.: 339,350

[22] Filed: Jan. 15, 1982

[30] Foreign Application Priority Data

Jan. 23, 1981 [GB] United Kingdom ............... 8102141

[51] Int. Cl.³ .............................................. A61K 31/24
[52] U.S. Cl. ..................................... 424/309; 424/311; 424/319; 424/287; 424/289; 424/295; 424/294; 424/293
[58] Field of Search ...................... 424/309, 311, 319

[56] References Cited

U.S. PATENT DOCUMENTS 3,154,578 10/1964 Kinnel ................................ 260/534

FOREIGN PATENT DOCUMENTS 2437833 4/1980 France ................................ 260/534

OTHER PUBLICATIONS

Chemical Abstracts vol. 78 (1973) Par. 93629k.
Chemical Abstracts vol. 94 (1981) Par. 90426n.

Primary Examiner—Elbert L. Roberts

[57] ABSTRACT

Use as agricultural fungicides of N-acyl-N-hydroxyalkanoic acid compounds of the formula

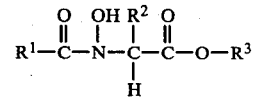

and salts thereof, wherein each of the symbols has an assigned meaning.

4 Claims, No Drawings

FUNGICIDES

DESCRIPTION OF THE INVENTION

It has been found that fungi, particularly mildews, are controlled by N-acyl-N-hydroxyalkanoic acid compounds of the formula

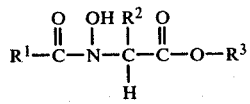

wherein $R^1$ is hydrogen or phenyl, $R^2$ is hydrogen or methyl and $R^3$ is hydrogen, methyl or ethyl, and salts thereof.

Preferably $R^1$ represents hydrogen.

Preferably $R^2$ represents methyl.

Preferably $R^3$ represents hydrogen and the compound is a salt.

A salt of the compound of Formula (I) may contain the monovalent anion in which the carboxyl group is ionized or the divalent anion in which the N-hydroxy group also is ionized. Polyvalent metal ions generally form salts with, or chelates derived from, the divalent anion, while monovalent metal ions can form mono- or divalent salts. Weak bases in general form only monovalent salts.

Typical metal salts include salts of lithium, sodium, potassium, magnesium, calcium, zinc, copper, lead, manganese or iron.

Typical non-metal salts include ammonium and substituted ammonium salts, for example those in which the cation has the formula $\oplus NR^4R^5R^6R^7$ in which each of $R^4$, $R^5$, $R^6$ and $R^7$ independently represents a hydrogen atom or an optionally substituted alkyl, cycloalkyl or aryl group having up to 12 carbon atoms. Optional substituents include for example halogen atoms and alkyl, alkoxy, haloalkyl, haloalkoxy, hydroxy, cyano, nitro, amino, carboxy, alkoxycarbonyl, phenyl and phenoxy groups, any alkyl moiety present preferably having up to 4 carbon atoms.

Further suitable substituted ammonium salts include those in which the nitrogen atom forms a part of a saturated or unsaturated ring, which may also contain one or more additional hetero-atoms, especially nitrogen, oxygen and/or sulphur atoms. Typical salts of this type are pyridinium, pyrrolidinium, piperidinium and morpholinium salts. Suitable salts thus include the salts of nitrogen bases, generally.

Further suitable salts include those with polymeric substances containing basic groups, such as ion exchange resins. Such salts can be especially useful in applications where insoluble materials are required.

Especially preferred for use in the method of the invention are the salts.

It will be appreciated that the compounds of Formula (I) contain an asymmetric carbon atom at the 2 position and hence will exist in two optically isomeric forms, which will not necessarily have equal fungicidal activity. Individual optical isomers, as well as deliberate and incidental mixtures of these isomers, such as racemic mixtures, are included within the scope of this invention.

The invention also provides a method for combating fungus at a locus, which comprises treating the locus, which may for example be plants subject to or subjected to fungal attack, seeds of such plants or the medium in which such plants are growing or are to be grown, with a fungicidally effective amount of a N-acyl N-hydroxyalkanoic acid compound as defined above. The present invention is of wide applicability in the protection of crop plants against fungal attack. Many organisms of the class Oomycetes are controled, for example *Phytophthora infestans, Bremia latucae,* and *Peronospora destructor.* Typical crops which can be protected include tobacco, potato, tomato, lettuce and cocoa. The present invention is of particular value in the protection of vines against fungal disease, such as downy mildew, *Plasmopara viticola,* because of the ability of the active compounds to provide a protective effect in those parts of the vine plant remote from the site of application. Thus, if the upper surfaces of leaves of a vine are sprayed, the plant becomes more resistant to fungal attack not only on the leaf undersurfaces (translaminar protection) but also on the plant surfaces emerging after the treatment. The active material can also be effective when applied to the stem or roots of the plant(s) to be protected. The duration of such protection is normally dependent on the individual compound selected, and also a variety of external factors, such as climate, whose impact is normally mitigated by the use of a suitable formulation.

A composition according to the invention preferably contains from 0.5 to 95% by weight of active ingredient, plus an inert carrier and/or a surfactant.

A carrier in a composition according to the invention is any inert material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example, a composition may contain at least two carriers, at least one of which is a surface-active agent.

Of particular interest in enhancing the duration of the protectant activity of the compounds of this invention is the use of a carrier which will provide a slow release of the fungicidal compound into the environment of the plant which is to be protected. Such slow-release formulations could, for example, be inserted in the soil adjacent to the roots of a vine plant, or could include an adhesive component enabling them to be applied directly to the stem of a vine plant.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain, in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–25% w active ingredient and 0–10% w of additives such as stabilisers, slow release modifiers and binding agents. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

The compositions may also contain other ingredients, for example other compounds possessing pesticidal, especially insecticidal, acaricidal, herbicidal or fungicidal, properties.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The compounds used in this invention can be synthesized by known procedures, for example via the corresponding nitrone as described in U.S. Pat. No. 3,154,578, or by suitable modifications of such procedures. However, an improved synthetic route has been discovered.

Accordingly, in another embodiment, the invention also provides a process for the preparation of a compound of the general formula I given above or a salt or an ester thereof, in which each of $R^1$ and $R^2$ have the meaning already given herein, which comprises reacting an ester of an acid of the general formula:

(II)

in which L represents a suitable leaving group, with hydroxylamine, to yield an ester of the acid of the general formula

(III)

optionally converting the resulting ester into the corresponding free acid or a salt thereof; and acylating the resulting compound with a suitable acylating agent; and if desired converting a resulting ester of the acid I into any required salt or ester or the free acid, by methods analogous to known methods.

Any leaving group which will be displaced by the hydroxylamine can be used. Suitable moieties include halogen, especially chlorine or bromine, atoms, and organic sulphonic acid groups of the formula $QSO_2O$— where Q is a hydrocarbon group, for example an alkyl, aryl or alkaryl group; typical groups of this type are the mesylate and tosylate groups. The reaction with hydroxylamine is perferably carried out in the presence of an acid acceptor, for example an amine, e.g. a trialkylamine.

The molar ratio of the reactants is not crucial. It may be convenient to use approximately stoichiometric quantities, and preferably at least one mole of hydroxylamine is used per mole of starting ester. An excess of hydroxylamine may be used as an acid acceptor. The reaction may for example be carried out at a temperature in the range of from 0° to 100° C., especially 15° to 70° C.

If desired, the hydroxylamine may be prepared in situ, for example by reaction of a hydroxylamine salt, such as hydroxylamine hydrochloride, with a base, for example an alkali metal hydroxide or alkoxide or an amine.

If desired, the ester III may be converted by known methods into the corresponding free acid or salt, which is then acylated. Preferably however it is the ester which is acylated.

Any suitable acylating agent may be used for reaction with the compound III, for example an anhydride, ester or acid halide derived from the acid $R^1COOH$. Mixed anhydrides are often useful. When $R^1$ represents a hydrogen atom, prefered acylating agents are the mixed anhydride of formic acid and acetic acid, which may be added as such, or formed in situ from a mixture of formic acid with acetic anhydride. Preferably at least one mole, for example from 1 to 5 moles, of acylating agent is used per mole of compound III. The reaction may for example be carried out at a temperature in the range of from 0° to 100° C., especially 15° to 70° C. In some cases, when using an ester III but requiring a salt or acid as the final product, it is possible to convert the ester group in the ester III into the free acid or a salt thereof in the same reaction vessel as the acylation, if the acylation step is carried out under conditions to which the ester group is not stable, for example under strongly acidic conditions.

An especially preferred method of preparing a free acid I or a salt thereof, involves the use of an ester in which the ester group is readily removed in the last step of the process. Such esters include for example the benzyl or, especially, the tertiary butyl ester, which groups are readily removed by hydrolysis or solvolysis either after the acylation step or simultaneously with the acylation step.

The starting ester of the acid II may be prepared in any suitable manner, for example by transesterification of any other ester of the acid II, or by esterification of the free acid or its acid halide. A preferred method of preparing the tertiary butyl ester comprises reaction of the free acid II with 2-methyl propane under acidic conditions. Suitable acid catalysts for use in this embodiment include, for example, mineral acids such as sulphuric acid, organic acids such as p-toluene sulphonic acid, and acidic ion exchange resins.

If it is desired to prepare a single optical isomer of the required compound, this may be done by using as starting material the appropriate chiral ester, and by conducting the various reaction steps under carefully controlled reaction conditions to avoid racemisation. The use of organic sulphonic acid leaving groups L is especially useful when working with chiral materials.

The following Examples illustrate the invention. In each case, the identities of the products and intermediates were confirmed by appropriate chemical and spectral analyses.

EXAMPLE I

N-formyl-N-hydroxyalanine (A) Synthesis via nitrone 1.0 mole of Z-benzaldoxime and 1.1 moles of alpha-bromopropionic acid were added to sodium ethoxide solution, prepared from 2 moles of sodium metal in 4 l of ethanol. The solution was heated for three hours at 65°–70° C. with stirring, cooled, and the resulting crystals of the sodium salt of N-benzylidene alanine N-oxide were filtered off. This product was dissolved in water and acidified with 2 N hydrochloric acid. The resulting acid nitrone crystals obtained were washed with ether and dried to yield the free acid, m.p.: 168°–170° C.

40 g of the acid nitrone was treated with 400 ml of formic acid and 80 ml of acetic anhydride and the resulting mixture was stirred at room temperature for 1 hour, then stirred a further ¾ hour, at 40°–45° C. The solvents were evaporated. The resultant oil was dissolved in water, washed with benzene and the aqueous layer neutralized by the addition of concentrated ethanolic sodium hydroxide solution. Ethanol was added slowly, and the resulting sodium salt of N-formyl-N-hydroxy alanine was filtered off. M.p.: 193°–195° C.

The free acid was conveniently obtained by passing the sodium salt down a Dowex-50 ion exchange column and eluting with water; the acid had a melting point of 77°–79° C.

(B) Synthesis via butylation

In a Parr hydrogenation flask was placed 0.33 mole of alpha-bromopropionic acid, 2 moles of isobutylene and 1.7 ml of concentrated sulphuric acid. The reaction mixture was shaken for 48 hours, then poured into a vigorously stirred solution of 20% sodium hydroxide, extracted with ether and dried to yield the crude tert.-butyl ester of alpha-bromopropionic acid.

Hydroxylamine was generated in methanol by the addition of 0.1 mole of sodium methoxide or hydroxide to 0.1 mole of hydroxylamine hydrochloride, followed by filtering off the sodium chloride, and was added to 0.1 mole of the above ester and 0.1 mole of triethylamine, in methanol, and the reaction mixture refluxed for 24 hours. After cooling, ether was added and the insoluble triethylamine hydrobromide filtered off. Evaporation of the solvents yielded a semi-solid product which was treated with petroleum ether (80–100) to yield N-hydroxyalanine tert. butyl ester, m.p.: 69°–70° C.

5 g of the ester was stirred at room temperature for 1 hour, with 40 ml of formic acid and 10 ml of acetic anhydride, then for a further 1 hour at 40°–45° C. The solvents were removed at low temperature, the residue dissolved in water and washed with benzene. The aqueous layer was treated with an equivalent of concentrated aqueous sodium hydroxide solution and ethanol slowly added to yield the sodium salt of N-formyl-N-hydroxyalanine, m.p.: 186°–187° C.

(C) Following such procedures, the further species of N-formyl-N-hydroxyamino acid derivatives of Formula I listed in Table I were prepared.

(D) Preparation of polyvalent metal salts

To a solution of 1 mole of N-hydroxy-N-formyl alanine in water was added, with stirring, 1 mole of lead acetate in water. The precipitate obtained was dried under high vacuum for several days to yield the lead salt, m.p.: 180° C. (dec).

Following a similar procedure the following salts of the same acid with other polyvalent ions were obtained:
Calcium, m.p.: above 300° C.
Copper, m.p.: 203°–205° C. (dec).

(E) Separation of optical isomers

Equimolar amounts of N-formyl-N-hydroxy alanine and strychnine were dissolved in a mixture of acetone and ethanol and stirred at a temperature of 4° C. for 24 hours. At the end of this time, the resulting precipitate was filtered off and treated with aqueous sodium hydroxide solution. The resulting precipitate was filtered off and the filtrate was freeze dried. The solid was then recrystalized from aqueous ethanol, to give the (+) isomer of the sodium salt of N-formyl-N-hydroxy alanine, which had a specific optical rotation in aqueous solution of +26.3°.

The above procedure was then repeated but using brucine instead of strychnine. The (−) isomer of the sodium salt of N-formyl-N-hydroxy alanine had a specific optical rotation of −25.2°.

(F) Direct synthesis from optically active starting materials.

0.35 mole of the S optical isomer of 2-mesyloxypropionic acid was dissolved in 25 ml of pyridine and 500 ml of t-butanol, and 65 g of phosphoryl chloride was added, with stirring, at $-5°$ C. After a further 30 minutes stirring at $-5°$ C., and a further 2 hours at $20°$ C., the mixture was poured into ice-water, and methylene chloride was added. The organic layer was washed successively with dilute hydrochloric acid, sodium bicarbonate, and water, and then evaporated to give a solid which was recrystalised from light petroleum ether to give (S) t-butyl 2-mesyloxypropionate.

0.05 mole of this ester was then dissolved in 25 ml of N-methylpyrrolidone and 0.051 mole hydroxylammonium chloride and 0.1 mole of triethylamine were added. The mixture was stirred overnight at $50°$ C., after which time it was poured into water, diethyl ether was added, the organic layer was evaporated down and the resulting product was purified by chromatography over silica using diethyl ether and methylene chloride as eluants. (R) t-butyl 2-hydroxyaminopropionate, having an optical rotation in chloroform solution of $+22.6°$, was obtained. This material could then be reacted with formic acid and acetic anhydride as described in (B) above, to give the required product.

EXAMPLE 2

Glasshouse Fungicide Evaluation (a) Antisporulant activity against vine downy mildew (*Plasmopara viticola;* P.v.a)

The test is a direct antisporulant one using a foliar spray. The lower surfaces of leaves of whole vine plants are inoculated by spraying with an aqueous suspension containing $10^5$ zoosporangia/ml 2 days prior to treatment with the test compound. The inoculated plants are kept for 24 hours in a high humidity compartment, and then 24 hours at glasshouse ambient temperature and humidity. The plants are then dried and infected leaves detached and sprayed on the lower surfaces with a solution of active material in 1:1 water/acetone containing 0.04% Triton X-155. The spraying is carried out with a moving track sprayer which delivers 620 l/ha, and the concentration of active material is calculated to give an application rate of 1 kg/ha. After drying, the petioles of the sprayed leaves are dipped in water and the leaves returned to high humidity for a further 96 hours incubation, followed by assessment. Assessment is based on the percentage of the leaf area covered by sporulation compared with that on control leaves.

(b) Translaminar activity against vine downy mildew (*Plasmopara viticola;* P.v.t)

The test is a translaminar protectant one using a foliar spray. The upper surfaces of leaves of whole vine plants are sprayed at a dosage of 1 kilogram of active material per hectare using a track sprayer as described under (a). The lower surfaces of the leaves are then inoculated, up to 6 hours after treatment, with the test compound, by spraying with an aqueous suspension containing $10^5$ zoosporangia/ml. The inoculated plants are kept for 24 hours in a high humidity compartment, 5 days at glasshouse ambient temperature and humidity and then returned for a further 24 hours to high humidity. Assessment is based on the percentage of the leaf area covered by sporulation compared with that on control leaves.

(c) Activity against vine grey mould (*Botrytis cinerea;* B.c.)

The test is a direct eradicant one using a foliar spray. The under-surface of the detached vine leaves are inoculated by pipetting ten large drops of an aqueous suspension containing $5 \times 10^5$ conidia/ml on to them. The inoculated leaves are kept uncovered overnight during which time the fungus has penetrated the leaf and a visible necrotic lesion may be apparent where the drop was made. The infected regions are sprayed directly with a dosage of 1 kg of active material per hectare using a track sprayer as described under (a). When the spray has dried the leaves are covered with petri dish lids and the disease allowed to develop under these humid conditions. The extent of the necrotic lesion beyond the original drop together with the degree of sporulation is compared with that on control leaves.

(d) Activity against tomato late blight (*Phytophthora infestans;* P.i.p)

The test measures the direct protectant activity of compounds applied as a foliar spray. Tomato plants, cultivar Outdoor Girl, 10-15 cms high, in monopots are used. The whole plant is sprayed at a dosage of 1 kilogram of active material per hectare using a track sprayer as described in (a). The plant is then inoculated up to 6 hours after treatment with the test compound, by spraying with an aqueous suspension containing $5 \times 10^3$ zoosporangia/ml. The inoculated plants are kept in high humidity for 3 days. Assessment is based on comparison between the levels of disease on the treated and control plants (e) Activity against apple powdery mildew (*Podosphaera leucotricha;* P.l.)

The test is a direct anti-sporulant one using a foliar spray. The upper surfaces of leaves of whole apple seedlings are inoculated by spraying with an aqueous suspension containing $10^5$ conidial/ml 2 days prior to treatment with the test compound. The inoculated plants are immediately dried and kept at glasshouse ambient temperatures and humidity prior to treatment. The plants are sprayed at a dosage of 1 kilogram of active material per hectare using a track sprayer as described under (a). After drying the plants are returned to a compartment at ambient temperature and humidity for up to 9 days, followed by assessment. Assessment is based on the percentage of the leaf area covered by sporulation compared with that on leaves of control plants.

(f) Activity against rice leaf blast (*Pyricularia oryzae;* P.o)

The test is a direct eradicant one using a foliar spray. The leaves of rice seedlings (about 30 seedlings per pot) are sprayed with an aqueous suspension containing $10^5$ spores/ml 20-24 hours prior to treatment with the test compound. The inoculated plants are kept overnight in high humidity and then allowed to dry before spraying at a dosage of 1 kg of active material per hectare using a track sprayer as described in (a). After treatment the plants are kept at $25°-30°$ C. and high humidity. Assessments are made 4-5 days after treatment and are based on the density of necrotic lesions and the degree of withering when compared with control plants.

The extent of disease control in all the above tests is expressed as a rating compared with a diluent sprayed control according to the criteria:

0 = less than 50% disease control
1 = about 50-80% disease control
2 = greater than 80% disease control A representative selection of N-acyl-N-hydroxy amino acid derivatives were evaluated using the above procedures, with the results set out in Table I, the compounds being identified by reference to the substituents in the formula given therein.

EXAMPLE 3

The protective fungicidal activity of selected compounds was evaluated by the following procedure. Test compounds were applied to the leaves of intact vine

TABLE I $$R^1CO-\underset{\underset{OX}{|}}{N}-\underset{\underset{R^2}{|}}{CH}-COOR^3$$

| COMPOUND | | | | FUNGICIDAL ACTIVITY | | | | | |
|---|---|---|---|---|---|---|---|---|---|
| $R^1$ | $R^2$ | $R^3$ | X | P.v.a. | P.v.t. | B.c. | P.i.p. | P.o. | P.l. |
| H | $CH_3$ | H | H | 2 | 2 | 0 | 0 | —(a) | 1 |
| H | $CH_3$ | $C_2H_5$ | H | 2 | 2 | — | — | — | — |
| H | $CH_3$ | Na | H | 2 | 0 | 2 | 0 | — | 0 |
| H | $CH_3$ | Na | Na | 2 | 0 | 0 | 0 | — | 0 |
| H | $CH_3$ | Li | H | 2 | 0 | 0 | 0 | 2 | 0 |
| H | $CH_3$ | K | H | 2 | 1 | 0 | 0 | 0 | 0 |
| H | $CH_3$ | Mg | | 2 | 0 | 0 | 0 | 0 | 0 |
| H | $CH_3$ | Ca | | 2 | 0 | 0 | 0 | 0 | 0 |
| H | $CH_3$ | Cu | | 2 | 2 | 0 | 0 | — | 1 |
| H | $CH_3$ | Pb | | 2 | 0 | 0 | 0 | — | 0 |
| H | $CH_3$ | Fe | | 2 | 0 | 0 | 0 | 0 | 0 |
| H | $CH_3$ | Mn | | 2 | 0 | 0 | 0 | — | 0 |
| H | $CH_3$ | Zn | | 2 | 0 | 0 | 0 | — | 0 |
| H | $CH_3$ | $NH_4^\oplus$ | H | 2 | 2 | — | — | — | 0 |
| H | $CH_3$ | $^\oplus NH_3.(CH_2)_2OH$ | H | 2 | 0 | — | — | — | 0 |
| H | $C_3$ | $^\oplus NH_2.[(CH_2)_2OH]_2$ | H | 2 | 0 | — | — | — | 0 |
| H | $CH_3$ | $^\oplus NH.[(CH_2)_2OH]_3$ | H | 2 | 1 | — | — | — | 0 |
| H | $CH_3$ | $H_2^\oplus N$-morpholinium | H | 2 | 1 | — | — | — | 0 |
| H | $CH_3$ | $^\oplus NH_3.(CH_2)_4CH_3$ | H | 2 | 0 | — | — | — | 0 |
| H | $CH_3$ | $^\oplus NH_3.(CH_2)_9.CH_3$ | H | 2 | 0 | — | — | — | 2 |
| H | $CH_3$ | $H_3N^\oplus$-cyclohexyl | H | 2 | 1 | — | — | — | 1 |
| H | $CH_3$ | $^\oplus NH_2(C_2H_5)_2$ | H | 2 | 1 | — | — | — | 0 |
| H | $CH_3$ | $^\oplus NH(C_2H_5)_3$ | H | 2 | 2 | — | — | — | 0 |
| H | $CH_3$ | $^\oplus N[CH_3.(CH_2)_3]_4$ | H | 2 | 0 | — | — | — | 2 |
| H | $CH_3$ | $H_2^\oplus N$-pyrrolidinium | H | 2 | 0 | 0 | 0 | — | 0 |
| H | $CH_3$ | $H_2^\oplus N$-piperidinium | H | 2 | 1 | 0 | 0 | — | 0 |
| H | $CH_3$ | Amberlite* CG400 | H | 2 | 0 | 0 | 0 | 0 | — |
| H | $CH_3$ | Amberlite* IRA193 | H | 2 | 2 | 0 | 0 | — | 0 |
| H | $CH_3$ | Amberlyst* A26 | H | 2 | 1 | 0 | 0 | — | 1 |
| H | $CH_3$ | Amberlyst* A21 | H | 2 | 1 | 0 | 0 | — | 0 |
| H | $CH_3$ | Dowex* 1-X8 | H | 2 | 0 | 0 | 0 | — | 0 |
| H | $CH_3$ | Zerolit* FX1P | H | 2 | 1 | 0 | 0 | — | 0 |
| $C_6H_5$ | H | H | H | 1 | 2 | 0 | 1 | — | — |
| H | H | $C_2H_5$ | H | 2 | 0 | 1 | 0 | — | — |
| H | H | Na | H | 2 | 2 | 0 | 2 | 0 | — |

*- ion exchange resins, Trade Marks.
(a)Not tested with respect to this organism.

plants (cv. Cabernet-Sauvignon) growing in 5" diam., pots in the glasshouse. The spray was composed of acetone and water (in 1:1 proportion), and a surfactant (Tween 20 Trade Mark) at 0.04% w/v.

Eight days after treatment the plants were inoculated with a suspension of spores of *Plasmopara viticola* (10³ zoosporangia/ml.). After a further eight days readings were made on the degree of sporulation on the abaxial surfaces of sprayed leaves.

From these readings, the reduction in sporulation attributable to the chemical treatment was calculated, and expressed as a percentage, by comparison with plants (controls) sprayed with the acetone/water/surfactant diluent. The results of these tests are given in Table II.

TABLE II

| Compound | Dose ppm | % sporulation reduction |
|---|---|---|
| N-formyl-N-hydroxy alanine | 500 | 100 |
| N-acetyl-N-hydroxy alanine | 1000 | 72.6 |
| N-formyl-N-hydroxy 2-amino- butanoic acid, sodium salt | 1000 | 50.8 |

We claim:

1. A method for controlling fungi at a locus to be protected which comprises applying to the locus a fungicidal amount of a compound of the formula:

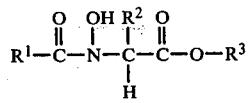

and salts thereof, wherein $R^1$ is hydrogen or phenyl, $R^2$ is hydrogen or methyl, and $R^3$ is hydrogen, methyl or ethyl.

2. A method according to claim 1 wherein $R^1$ is hydrogen.

3. A method according to claim 2 wherein $R^2$ is methyl.

4. A method according to claim 3 wherein $R^3$ is hydrogen and the compound is in the form of a salt.

* * * * *